(12) United States Patent
Nouvelle

(10) Patent No.: US 8,818,736 B2
(45) Date of Patent: Aug. 26, 2014

(54) ALLOCATING OIL PRODUCTION FROM GEOCHEMICAL FINGERPRINTS

(75) Inventor: Xavier Nouvelle, Les Matelles (FR)

(73) Assignee: Schlumberger Technology Corporation, Sugar Land, TX (US)

( * ) Notice: Subject to any disclaimer, the term of this patent is extended or adjusted under 35 U.S.C. 154(b) by 357 days.

(21) Appl. No.: 13/307,080

(22) Filed: Nov. 30, 2011

(65) Prior Publication Data

US 2013/0138360 A1  May 30, 2013

(51) Int. Cl.
*G01N 31/00* (2006.01)
*G01N 30/02* (2006.01)

(52) U.S. Cl.
USPC .......................................... 702/23; 73/23.38

(58) Field of Classification Search
CPC ........................ G01N 30/8686; G01N 33/2823
USPC ......... 702/23–25, 30–32, 189, 193–194, 196;
73/1.02, 1.06, 19.01–19.02, 23.2,
73/23.22, 23.35–23.36, 23.38; 703/2, 5, 9,
703/12
See application file for complete search history.

(56) References Cited

PUBLICATIONS

McCaffrey et al., Geochemical Allocation of Commingled Oil Production and/or Commingled Gas Production from 2-6 Pay Zones, Jun. 8-11, 2010, AAAPG Hedberg Conference, Vail, Colorado, 5 pp.*

Boehm, et al., "Application of petroleum hydrocarbon chemical fingerprinting and allocation techniques after the Exxon Valdez oil spill", Marine Pollution Bulletin, vol. 34 (8), Aug. 1997, pp. 599-613.

Chang, et al., "Geochemical surveillance of the Linnan Oil Field with oil fingerprinting", Energy, Exploration & Exploitation, vol. 28 (4), 2010, pp. 279-293.

Hwang, et al., "Allocation of commingled pipeline oils to field production", Organic Geochemistry, vol. 31 (12), Dec. 2000, pp. 1463-1474.

Kaufman, et al., "A New Technique for the Analysis of Commingled Oils and Its Application to Production Allocation Calculations", 16th Annual Convention Proceedings, vol. 2, 1987, pp. 247-268.

Kaufman, et al., "Gas Chromatography as a development and production tool for fingerprinting oils from individual reservoirs: applications in the Gulf of Mexico", Proceedings of the 9th Annual Research Conference of the Society of Economic Paleontologists and Mineralogists, D. Schumaker and B. F. Perkins, Ed., New Orleans, 1990, pp. 263-282.

Wen, et al., "The application of gas chromatography fingerprint technique to calculating oil production allocation of single layer in the commingled well", Chinese Journal of Geochemistry, vol. 24 (3), Jul. 2005, pp. 257-261.

* cited by examiner

*Primary Examiner* — Toan Le
(74) *Attorney, Agent, or Firm* — Colin Wier; Rodney Warfford

(57) ABSTRACT

Example embodiments include one or more of a method, computing device, computer-readable medium and system for allocating oil production from geochemical fingerprints. In an example embodiment, a method may include providing a known mixture comprising known proportions of a plurality of end-members; providing an unknown mixture comprising unknown proportions of the end-members; performing a chromatographic analysis of each of the known mixture, the end-members, and the unknown mixture; determining a plurality of peak ratios, and prior peak ratio qualities related to the peak ratios, using the chromatographic analysis; and estimating an estimate of the unknown proportions of the end-members using the peak ratios, the prior peak ratio qualities, and the known proportion of the end-members.

20 Claims, 6 Drawing Sheets

ALLOCATING OIL PRODUCTION FROM GEOCHEMICAL FINGERPRINTS

BACKGROUND

Interpretation of fingerprints obtained by gas chromatography (GC) of crude oils for allocating commingled production from multiple zones in a single well, or for allocating contributions from different wells, may result in cost savings relative to production logging. Also, it may be used to monitor production. However, the accuracy of the results may depend on the underlying method and the mathematics.

The use of GC fingerprints dates has been described in [1] Kaufman R. L., Ahmed A. S. and Elsinger R. J., Gas Chromatography as a development and production tool for fingerprinting oils from individual reservoirs: applications in the Gulf of Mexico: In: Proceedings of the 9th Annual Research Conference of the Society of Economic Paleontologists and Mineralogists. (D. Schumaker and B. F. Perkins, Ed.), New Orleans, 1990, pp. 263-282; and [2] Kaufman R. L., Ahmed A. S., Hempkins W. B., A new technique for the analysis of commingled oils and its application to production allocation calculations. Proceedings of the Sixteenth Annual Convention of the Indonesia Petroleum Association, 1987, pp. 247-268.

SUMMARY

Example embodiments may include one or more of a method, computing device, computer-readable media and system for allocating oil production from geochemical fingerprints. In an example embodiment, a method, computing device, computer-readable media, and system may enable providing a known mixture comprising known proportions of a plurality of end-members; providing an unknown mixture comprising unknown proportions of the end-members; performing a chromatographic analysis of each of the known mixture, the end-members, and the unknown mixture; determining a plurality of peak ratios, and prior peak ratio qualities related to the peak ratios, using the chromatographic analysis; and estimating an estimate of the unknown proportions of the end-members using the peak ratios, the prior peak ratio qualities, and the known proportion of the end-members.

BRIEF DESCRIPTION OF THE DRAWINGS

Implementations of various technologies will hereafter be described with reference to the accompanying drawings. It should be understood, however, that the accompanying drawings illustrate only the various implementations described herein and are not meant to limit the scope of various technologies described herein.

DETAILED DESCRIPTION

Methods Using Absolute Measurements

Figure 1:
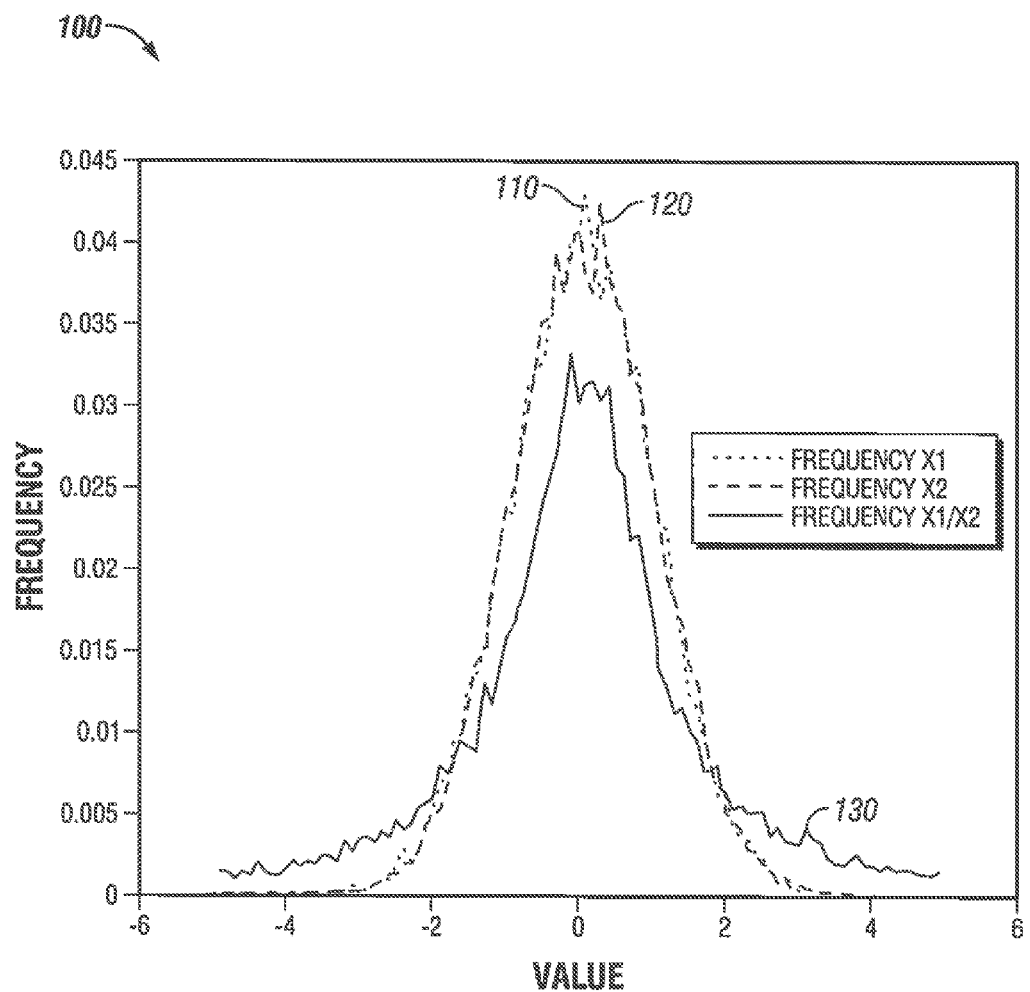
FIG. 1 shows a chart of an example distribution of realizations of two normally distributed variables X1 and X2 according to an example embodiment.

Various methods may be applied to GC fingerprint measurements for allocating commingled oils. Certain methods may include using absolute measurements. As an example, a first class of methods may use peak heights to solve the numerical systems given by the following Equation (1):

$$p_i^M = x_{EM1}^M \cdot p_i^{EM1} + x_{EM2}^M \cdot p_i^{EM2} + \ldots + x_{EMN}^M \cdot p_i^{EMN} \quad \text{Equation (1)}$$

In Equation (1):
$p_i^M$: Massic fraction of compound i in the mixture M;
$x_{EMk}^M$: Massic fraction of end member EMk in the mixture M;
$p_i^{EMk}$: Massic fraction of compound i in the end member k;

The sum of the mass fractions of the end-members equals one. This information may be used to reduce the number of unknowns.

Given that, for each sample S:

$$p_i^S = \frac{\gamma_i \cdot H_i}{m_S^{Injected}} \quad \text{Equation (2)}$$

In Equation (2):
$H_i$: Peak measurement (height, area) of the compound i;
$m_S^{Injected}$: Mass of sample S injected in the chromatography device;
$\gamma_i$: response factor of compound i;

Equation (1) becomes:

$$\frac{H_i^M}{m_M^{Inj}} = x_{EM1}^M \cdot \frac{H_i^{EM1}}{m_{EM1}^{Inj}} + x_{EM2}^M \cdot \frac{H_i^{EM2}}{m_{EM2}^{Inj}} + x_{EM3}^M \cdot \frac{H_i^{EM3}}{m_{EM3}^{Inj}} + \ldots \quad \text{Equation (3)}$$

This system of linear equations (one equation for each compound i) is under-determined. That is, the unknowns include the fractions of the end-members, as well as the injected masses of each sample.

Some methods may ignore the injected masses by setting them all to one. However, such practice may involve a rigorous analytical protocol in order to obtain desired reproducibility in the injected masses. Given that such amounts may be very low (in certain cases, approximately 0.1 µl), it may be difficult to ensure this condition.

Other methods may use calibration compounds. A calibration compound may include a chemical species not naturally present in crude oils. It may be added in known proportions in the samples before each injection in the chromatography device. Using Equation (2), it may be possible to solve the under-determination in Equation (3). Such methods may have a weakness, in that an error in the measurement on the calibration compound may introduce a systematic bias in the calculations.

Methods using single peak measurements may present another weakness: the relative amounts of the lightest hydrocarbons in a crude oil and the heaviest compounds might not be accurate. There are several possible explanations, including: (a) the possibility that compositional gradients in the reservoirs; (b) evaporation of the lightest hydrocarbons during the manipulations or during the stocking; (c) differences in mobility between light and heavy compounds during production; (d) blocking of the heaviest hydrocarbons in the injection or the chromatographic column devices, etc. The discrepancies between the light and the heavy hydrocarbons may propagate in the systems of equations, which may lead to uncertainty in the results.

Methods Using Relative Measurements

Certain aspects related to methods that use absolute measurements may be addressed by a second class of methods.

Some methods that involve relative measurements may use peak ratios rather than single peak measurements. Each peak ratio may be formed by the measurements of a plurality of peaks that are within a predetermined range with respect to each other in a plurality of chromatograms. For example, the predetermined range may range from approximately two consecutive peaks to half the distance between two consecutive n-alkanes. As the position of a peak in the chromatograms may be proportional to the molar weight of the corresponding compound, peaks with approximately similar weights could be used in the peak ratios.

One or more synthetic mixtures with known proportions of an end-member may be prepared and analyzed with the other samples (e.g., the end-members and the mixtures to be characterized). The synthetic mixtures may include a plurality of end-members. Using the synthetic mixtures, it may then be possible to plot the evolution of a selection of peak ratios according to the amounts of each end-member. As a result, the amounts of end-members according to the peak ratios can be interpolated. This interpolation can be used to evaluate the proportions of end-members in the mixtures to be characterized.

Methods that use peak ratios may exhibit one or more of the following:

- In some cases, interpolation might not be consistent with the theory. As a result, a certain number of synthetic mixtures might be used to cause the interpolated values to remain accurate.
- Values corresponding to peak ratios may be more uncertain than single peak ratios. For example, the division operator could drastically propagate uncertainty from both peaks involved in the ratio. A follow-up of each peak ratio may be performed to estimate their quality. So in practice, a plurality of chosen peak ratios may be involved in the calculations. Statistically, in certain circumstances, this situation (uncertainty on the measurements, weak number of measurements) might not be favorable to obtaining accurate results.

Example Embodiments Using Peak Ratios

In view of certain aspects associated with the above-described methods for allocating oil production from geochemical fingerprints, there may be a need for methods of allocating oil production from geochemical fingerprints that provide more accurate estimation of corresponding uncertainty than conventional methods.

An example method may combine at least one chromatographic analysis of at least one end member, at least one mixture of the end-member(s) to be characterized, and at least one synthetic mixture with known proportions of the end-members. The method may include using measurements related to chromatograms in a procedure to determine proportions of each end-member in the mixtures, and their related uncertainty. Instead of using single peak measurements, example embodiments may use peak ratios, and may take into account a plurality of the peak ratios available. The foregoing may provide a method based on maximum likelihood that combines the simultaneous resolution of the equations directly derived from theory and an estimation of the peak ratio uncertainties.

Example embodiments may use peak ratios rather than absolute measurements. As compared to certain other methods that use peak ratios, example embodiments may develop and adapt the equations given by theory to obtain results. In addition, example embodiments might take into consideration a whole set of peak ratios, rather than a particular set of chosen peak ratios. Indeed, an example embodiment may exploit the fact that a large number of measurements that are statistically well-managed may reduce uncertainty in the results.

From equation (3) above, the ratio of peak i and peak j can be expressed as Equation (4) below:

$$\frac{H_i^M}{H_j^M} = \frac{x_{EM1}^M \cdot \frac{m_{EMN}^{Inj}}{m_{EM1}^{Inj}} \cdot H_i^{EM1} + x_{EM2}^M \cdot \frac{m_{EMN}^{Inj}}{m_{EM2}^{Inj}} \cdot H_i^{EM2} + \ldots + x_{EMN}^M \cdot H_i^{EMN}}{x_{EM1}^M \cdot \frac{m_{EMN}^{Inj}}{m_{EM1}^{Inj}} \cdot H_j^{EM1} + x_{EM2}^M \cdot \frac{m_{EMN}^{Inj}}{m_{EM2}^{Inj}} \cdot H_j^{EM2} + \ldots + x_{EMN}^M \cdot H_j^{EMN}}$$

Equation (4)

The unknowns in such a system of equations may include:
- the amounts of each end-member in the mixture; and
- the relative injected masses of each end-member in the chromatography device.

For a synthetic mixture, however, the unknown variables might only include the relative injected masses of the end-members into the chromatograph device. Since these variables may be constant for each couple {i,j} of peaks, they can be optimized using at least N−1 couples of peaks, assuming that the amount of each end-member in the synthetic mixture must be greater than zero. However, in an example embodiment, the highest number of peak ratios can be used to reinforce the statistical significance of the results.

On the other hand, certain peak ratios may be more accurate than others. In addition, certain peak heights can be used several times. The foregoing circumstances may introduce a bias into the results. Accordingly, a quality related to each peak ratio may be introduced to provide a better estimation of the unknown variables.

Prior Quality of Peak Ratios
Weight Associated with Each Peak Ratio

The quality associated with each peak ratio may be inversely proportional to the number of occurrences that each peak is used in the whole system of equations:

$$\text{Weight}_{Hi/Hj} = \frac{2}{n_{Hi} + n_{Hj}}$$

Equation (5)

In Equation (5) above, $n_{Hk}$ may represent a number of occurrences that the peak k may be used in the whole set of peak ratios.

Prior Uncertainty Associated with Each Peak Ratio

In addition, the quality may be linked to the uncertainty on each peak ratio. Given the standard deviation $\sigma_{Hi}$ and $\sigma_{Hj}$ of peak measurements Hi and Hj, the standard deviation of their ratio can be approximated using Equation (6) below:

$$(\sigma_{Hi/Hj})^2 = \frac{1}{(Hj)^2}\left[(\sigma_{Hi})^2 + \left(\frac{Hi}{Hj}\right)^2 \cdot (\sigma_{Hj})^2\right]$$

Equation (6)

Use of Additional Chromatographic Analyses

In an example embodiment, one or more additional chromatographic analyses of the same sample can be performed (such additional chromatographic analyses may be denoted as $N_{dupl} \in I$ in the equations below). These additional chromatographic analyses can be used to determine a prior uncertainty on a peak measurement k (e.g., each peak measurement k):

$$\sigma_{Hk} = \sqrt{\frac{1}{N_{dupleI}} \cdot \sum_{i=1}^{N_{dupleI}} (H_{k_i} - \overline{H}_{k\,Sample\,I})^2} + \text{Noise} \qquad \text{Equation (7)}$$

In Equation (7):

$H_{k_i}$: Peak measurement k, normalized on the additional chromatographic analyses, for the chromatographic analysis i, additional chromatographic analysis related to sample I;

$\overline{H}_{k_{Sample\,I}}$: Average value of the peak measurement k for all the additional chromatographic analysis related to sample I;

If additional chromatographic analyses were run for M samples, then the prior uncertainty on a peak measurement may be given as:

$$\sigma_{Hk} = \sqrt{\frac{\sum_{I=1}^{M}\left[\cdot \sum_{i=1}^{N_{dupleI}} (H_{k_i} - \overline{H}_{k\,Sample\,I})^2\right]}{\sum_{I=1}^{M} N_{dupleI}}} + \text{Noise} \qquad \text{Equation (8)}$$

The term "Noise" may be introduced to prevent an unrealistic peak uncertainty estimation. In certain situations, there may be a large number of peak measurements (e.g., several hundred), compared to a very low number of possible additional chromatographic analyses (if any) that can be used to estimate the uncertainty on each peak ratio. Under certain circumstances, it may be the case that the uncertainty $\sigma_{Hk}$ on certain peaks is approximately close to zero. To prevent such a situation, the additional term "Noise" may be used. In an example embodiment, "Noise" may be calculated from the normalized chromatograms of the samples. According to another example embodiment, a signal processing method can be used to estimate "Noise."

Use of Default Values

If there are no additional chromatographic analyses, then default parameters may be used. Each peak height prior uncertainty may be represented as:

$$\sigma_{Hk} = \text{Noise} \qquad \text{Equation (9)}$$

Prior Quality

The prior quality associated with a peak ratio may be determined using Equations (5) and (6) above:

$$\text{Qual}^0_{Hi/Hj} = \frac{\text{weight}_{Hi/Hj}}{\sigma_{Hi/Hj}} \qquad \text{Equation (10)}$$

Estimation of the Relative Injected Amounts of End-members and Posterior Peak Ratio Uncertainties The estimation procedure may include one or more of the following, as described in more detail below.

Optimization of the Relative Injected Amounts of End-members

Upon providing the prior quality $\text{Qual}_{Hi/Hj}^0$ of each peak ratio, the relative injected masses of end-members in the chromatograph devices may be evaluated using at least one synthetic mixture. Although example embodiments herein may be described with respect to one synthetic mixture, it should be understood that a plurality of synthetic mixtures could also be used.

An optimization procedure may be involved for this purpose. In an example embodiment, the optimization procedure may be based on the minimization of the objective function set forth in Equations (11) and (12) below:

$$f\left(\frac{m_{EMN}^{Inj}}{m_{EM1}^{Inj}}; \frac{m_{EMN}^{Inj}}{m_{EM1}^{Inj}}; \ldots \mid \text{Qual}^0_{Hi/Hj}\right) = \qquad \text{Equation (11)}$$

$$\sum_{\forall(i;j)} \ln\left\{1 + \frac{1}{2}\left[\text{Qual}^0_{Hi/Hj} \cdot \left(\left(\frac{H_i^M}{H_j^M}\right)_{Real} - HiMHjMMod2\right)\right]\right\}$$

with:

$$\left(\frac{H_i^M}{H_j^M}\right)_{Mod} = \frac{x_{EM1}^M \cdot \frac{m_{EMN}^{Inj}}{m_{EM1}^{Inj}} \cdot H_i^{EM1} + x_{EM2}^M \cdot \frac{m_{EMN}^{Inj}}{m_{EM2}^{Inj}} \cdot H_i^{EM2} + \ldots + x_{EMN}^M \cdot H_i^{EMN}}{x_{EM1}^M \cdot \frac{m_{EMN}^{Inj}}{m_{EM1}^{Inj}} \cdot H_j^{EM1} + x_{EM2}^M \cdot \frac{m_{EMN}^{Inj}}{m_{EM2}^{Inj}} \cdot H_j^{EM2} + \ldots + x_{EMN}^M \cdot H_j^{EMN}} \qquad \text{Equation (12)}$$

The example objective function above is not a classical least square function. The reason for such a choice may be motivated by the following observations:

In certain cases, some peak heights or peak areas measurements may be different from their expectation (i.e., their true value); for example, in certain chromatograms, some errors in peak attributions may arise and the presence of neighbor compounds in the chromatograms can perturb the measurement. In other terms, the assumption that peak measurements are normally distributed can be wrong.

In the case where the peak measurements have been checked and sorted, they can approach a normal distribution. However, the ratio of two normally distributed variables might not be distributed as a Gaussian function, but instead as a Cauchy (or Lorentzian) function.

FIG. 1 shows a chart 100 that presents the distribution of 20000 realizations of two normally distributed variables X1 110 and X2 120. It also presents the distribution of their ratio X1/X2 130.

The classical least square objective function does not obey the maximum likelihood. Furthermore, the use of classical least squares amplifies the importance of peak ratio outliers, which may be quite frequent for such heavy tailed distribution.

For a Cauchy distribution, the probability associated with each difference between real and expected peak ratio values can be given as Equation (13) below:

$$\text{Prob}\left[\left(\frac{H_i^M}{H_j^M}\right)_{Real} - \left(\frac{H_i^M}{H_j^M}\right)_{Mod}\right] \sim \qquad \text{Equation (13)}$$

$$\frac{1}{1 + \frac{1}{2 \cdot \sigma^2_{Hi/Hj}}\left(\left(\frac{H_i^M}{H_j^M}\right)_{Real} - \left(\frac{H_i^M}{H_j^M}\right)_{Mod}\right)^2}$$

In the general framework of the maximum likelihood estimation, the optimized parameters may be those which maximize the probability on the whole set of peak ratios, as set forth in Equation (14) below:

$$\text{Prob} \propto \prod_{\{i;j\}}^{Nratios} \left[1 + \frac{1}{2 \cdot \sigma_{Hi/Hj}^2}\left(\left(\frac{H_i^M}{H_j^M}\right)_{Real} - \left(\frac{H_i^M}{H_j^M}\right)_{Mod}\right)^2\right]^{-1} \quad \text{Equation (14)}$$

Maximizing this probability may be equivalent to minimizing the negative of its logarithms:

$$\sum_{\forall \{i;j\}} \ln\left\{1 + \frac{1}{2 \cdot \sigma_{Hi/Hj}^2} \cdot \left[\left(\frac{H_i^M}{H_j^M}\right)_{Real} - \left(\frac{H_i^M}{H_j^M}\right)_{Mod}\right]^2\right\} \quad \text{Equation (15)}$$

This objective function uses a logarithm and may be safer than least squares, since it may be inherently resistant to being thrown off by outliers among the data points.

The minimization of Equation (11) can be performed using classical methods for parameter optimization for non-linear models, including, for example, Nelder and Mead Simplex method, evolution strategies, etc.

If several synthetic mixtures are available, they may all be used at the same time to reinforce the accuracy of the method.

Optimization of the Qualities Related to Each Peak Ratio

Once the relative injected masses are estimated, it is possible to evaluate the difference between the real peak ratios and the estimated peak ratios according to Equation (12) above. If one assumes that these differences are coherent with the qualities involved in the optimization of the estimated injected masses of end-members in the chromatography device, a second optimization loop may be performed. This second optimization loop may include the optimization of the estimated injected masses of end-members. An example method is detailed below.

1) Definition of the a prior quality $\text{Qual}_{Hi/Hj}^{step\ 0}, \forall\{i;j\}$ as detailed in (10)
2) Optimization of the injected end-member masses: minimization of (11)
3) Second step Optimization:
   (a) Using (12), calculation of $$\left(\frac{Hi}{Hj}\right)_{Mod},$$

(b) Calculation of:

$$\sigma_{Hi/Hj}^{step\ k} = \frac{1}{2}\left(\sqrt{\frac{1}{NM}\sum_{n}^{NM}\left(\left(\frac{Hi}{Hj}\right)_{Mod}^n - \left(\frac{Hi}{Hj}\right)_{Real}^n\right)^2} + \sigma_{Hi/Hj}^{step\ k-1}\right) \quad \text{Equation (16)}$$

In Equation 16 above, NM represents a number of synthetic mixtures available,
   a—Calculation of $\text{Qual}_{Hi/Hj}^{step\ k}$ according to (10)
   b—Go back to 2) and repeat until the average difference between $\sigma_{Hi/Hj}^{step\ k}$ and $\sigma_{Hi/Hj}^{step\ k-1}$ is less than a predetermined threshold (e.g., 1% in Equation (17) below):

$$\frac{1}{N_{ratios}} \cdot \sum_{\{i;j\}}\left|\frac{\sigma_{Hi/Hj}^{step\ k} - \sigma_{Hi/Hj}^{step\ k-1}}{\sigma_{Hi/Hj}^{step\ k-1}}\right| < 0.01 \quad \text{Equation (17)}$$

At the end of the above method, the two following objectives may be fulfilled:
   The relative injected masses of end-members are optimized according to the maximal likelihood,
   The comparison of calculated peak ratios and measured peak ratios are compatible with the uncertainties used in the optimization procedure.

Estimation of the end-member fractions in the mixtures to characterize

Once the injected amounts of each end-member in the chromatography device have been estimated using the procedure detailed above, they can be used to evaluate the end-member fractions in the unknown mixtures.

The end-member fractions of an end-member in each unknown mixture X may be obtained by minimizing the objective function shown in Equations (18) and (19) below:

$$f(x_{EM1}^X, x_{EM2}^X, \ldots, x_{EMN}^X | \text{Qual}_{Hi/Hj}^k) = \quad \text{Equation (18)}$$

$$\sum_{\forall\{i;j\}} \ln\left\{1 + \frac{1}{2}\left[\text{Qual}_{Hi/Hj}^k \cdot \left(\left(\frac{H_i^X}{H_j^X}\right)_{Real} - HiXHjX\text{Mod2}\right)\right]\right\}$$

With:

$$\left(\frac{H_i^X}{H_j^X}\right)_{Mod} = \frac{x_{EM1}^X \cdot \frac{m_{EMN}^{Inj}}{m_{EM1}^{Inj}} \cdot H_i^{EM1} + x_{EM2}^X \cdot \frac{m_{EMN}^{Inj}}{m_{EM2}^{Inj}} \cdot H_i^{EM2} + \ldots + x_{EMN}^X \cdot H_i^{EMN}}{x_{EM1}^X \cdot \frac{m_{EMN}^{Inj}}{m_{EM1}^{Inj}} \cdot H_j^{EM1} + x_{EM2}^X \cdot \frac{m_{EMN}^{Inj}}{m_{EM2}^{Inj}} \cdot H_j^{EM2} + \ldots + x_{EMN}^X \cdot H_j^{EMN}} \quad \text{Equation (19)}$$

Since the sum of the end-member fractions may be made to equal to one, the parameter $x_{EMN}^X$ does not participate to the optimization procedure. It may be simply replaced by the expression:

$$x_{EMN}^X = 1 - \sum_{i=1}^{N-1} x_{EMi}^X \quad \text{Equation (20)}$$

The objective function above has the same form as the former one used to evaluate the injected masses of end-members since the peak ratios remain Cauchy distributed. The qualities $\text{Qual}_{Hi/Hj}^k$ are also given by the former optimization procedure on the injected masses of end-member.

Uncertainty Calculations

A bootstrap procedure may be implemented in order to propose an estimate of the uncertainties on the results of the methods described above. The following example bootstrap procedure may be used for this purpose:

From the dataset of the plurality of peak measurements available (referred to herein as $D_{(0)}^S$), a dataset $D_{(1)}^S$ may be generated. In an example embodiment, these N peak measurements may be randomly drawn with replacement from $D_{(0)}^S$. $D_{(0)}^S$ and $D_{(1)}^S$ could include the same number of peak measurements. However, in some embodiments, $D_{(0)}^S$ and $D_{(1)}^S$ may include a different number of peak measurements.

From the dataset $D_{(1)}^S$, another dataset of peak ratios may be built (the built dataset may be referred to herein as a "synthetic dataset"). In an example embodiment, only the peak ratios which exist in $D_{(0)}^S$, and which are formed by a plurality of peaks available in $D_{(1)}^S$ (e.g., two peaks) may be present in the synthetic dataset. In another example embodiment, redundancies of peak measurements in $D_{(1)}^S$ may be considered as distinctive measurements.

An optimization procedure may thus be carried out using a synthetic dataset, and the results obtained by performing the optimization procedure using the synthetic dataset may be stored.

This bootstrap procedure may be repeated a plurality of times (e.g., in an example embodiment, the procedure may be repeated approximately one hundred times).

Upon performing the bootstrap procedure, the covariance matrix of the results obtained by performing the optimization procedure using the synthetic dataset may be calculated. In an example embodiment, the covariance matrix may be determined as follows:

$$\text{Cov}_{ij} = \frac{1}{N}\sum_{k=1}^{N}\left((x_{EMi}^X)_{D_{(k)}^S} - (x_{EMi}^X)_{D_{(0)}^S}\right)\left((x_{EMj}^X)_{D_{(k)}^S} - (x_{EMj}^X)_{D_{(0)}^S}\right) \quad \text{Equation (21)}$$

The diagonal elements may provide an estimation of the variance on each end-member fraction in the unknown mixture X, while the non-diagonal elements of the covariance matrix can be used to provide an estimation of the possible correlations between the fractions of the end-members.

Figure 2:
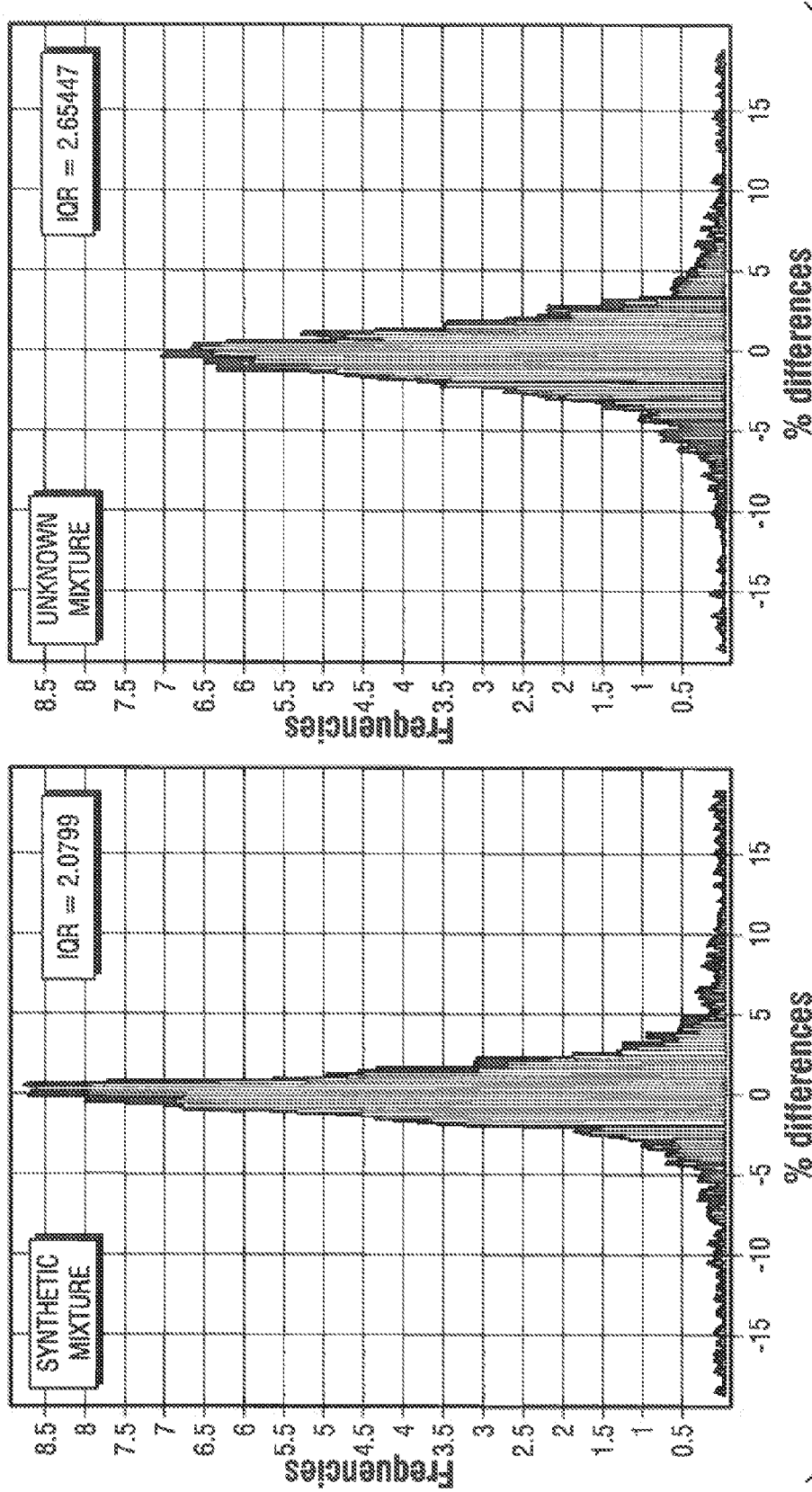
FIG. 2 shows a plot that compares real peak ratios to theoretical peak ratios according to an example embodiment.

Once the end-member fractions have been estimated, it is also possible to calculate the theoretical peak ratios of each mixture, and compare the theoretical peak ratios to the real peak ratios. The distribution of their differences can also be plotted to control the quality of the overall process (e.g., using a distribution histogram). This may be of particular interest when these distributions related to the unknown mixtures are compared to the distributions related to the synthetic mixtures, as this may provide a method to check the extent to which the unknown mixtures are real mixtures of the end-members. FIG. 2 shows a plot 200 that compares real peak ratios to theoretical peak ratios according to an example embodiment.

Figure 3A:
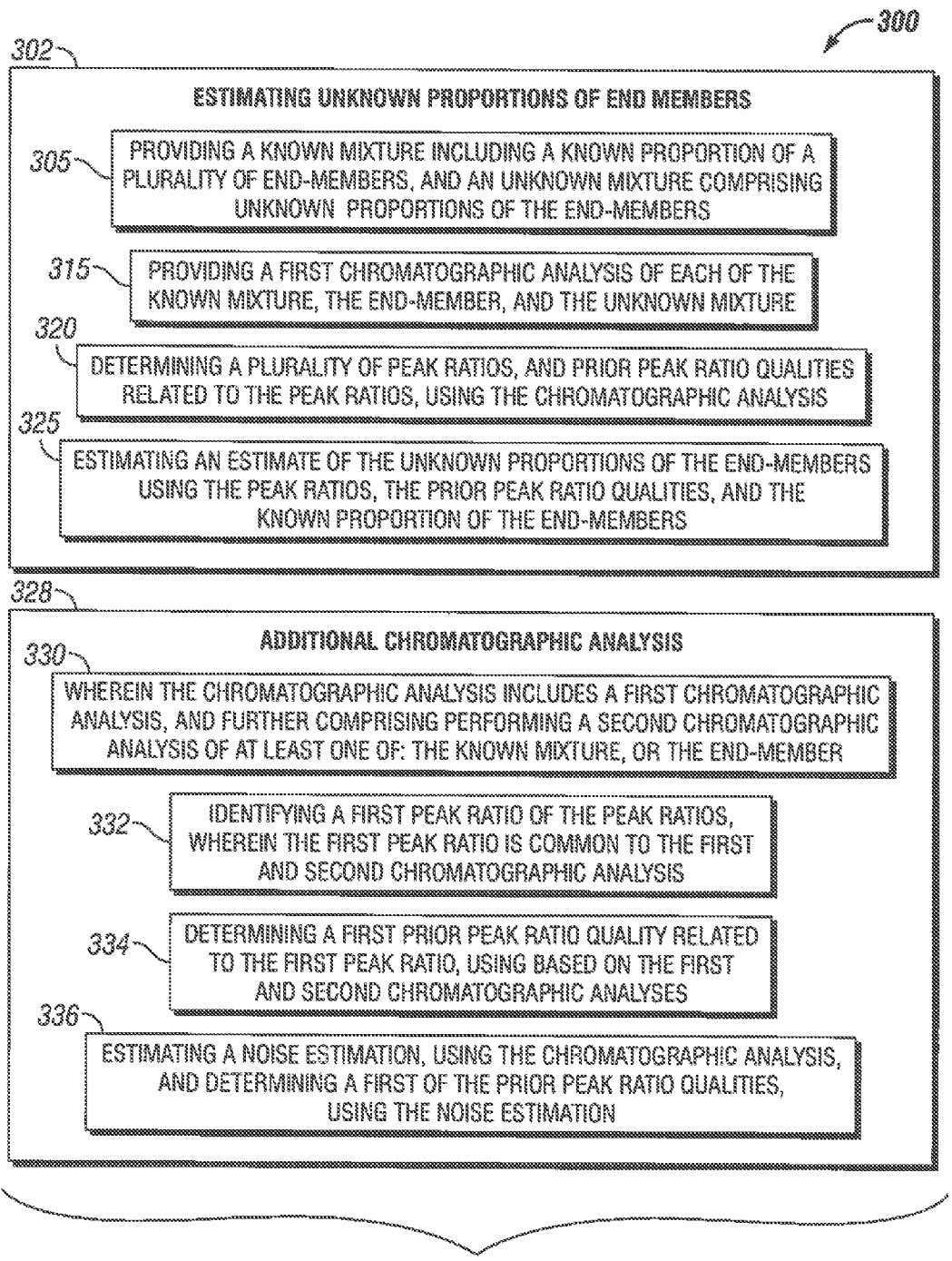
FIG. 3 shows a flow diagram of a method according to an example embodiment.
Figure 3B:
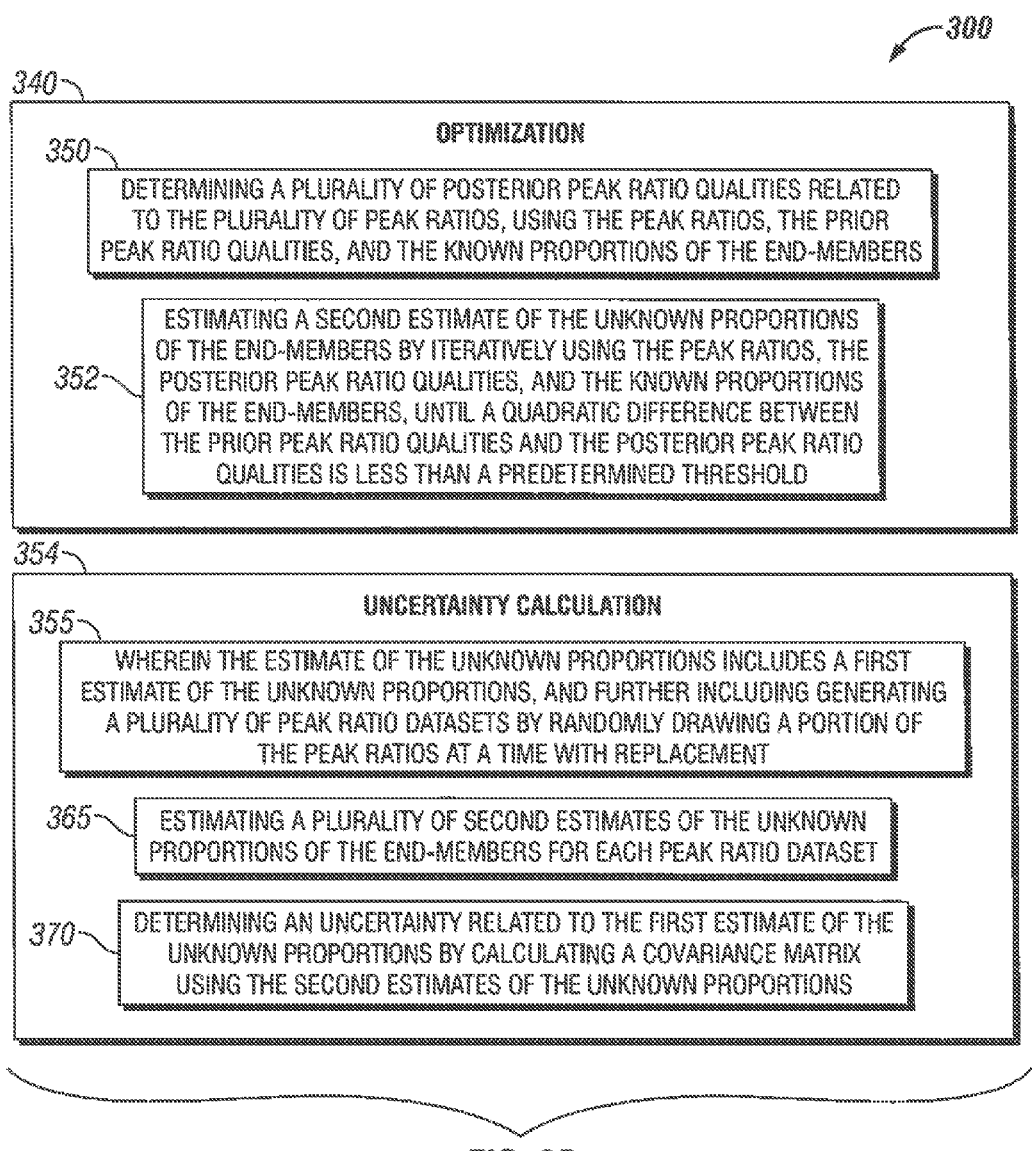
Figure 3C:
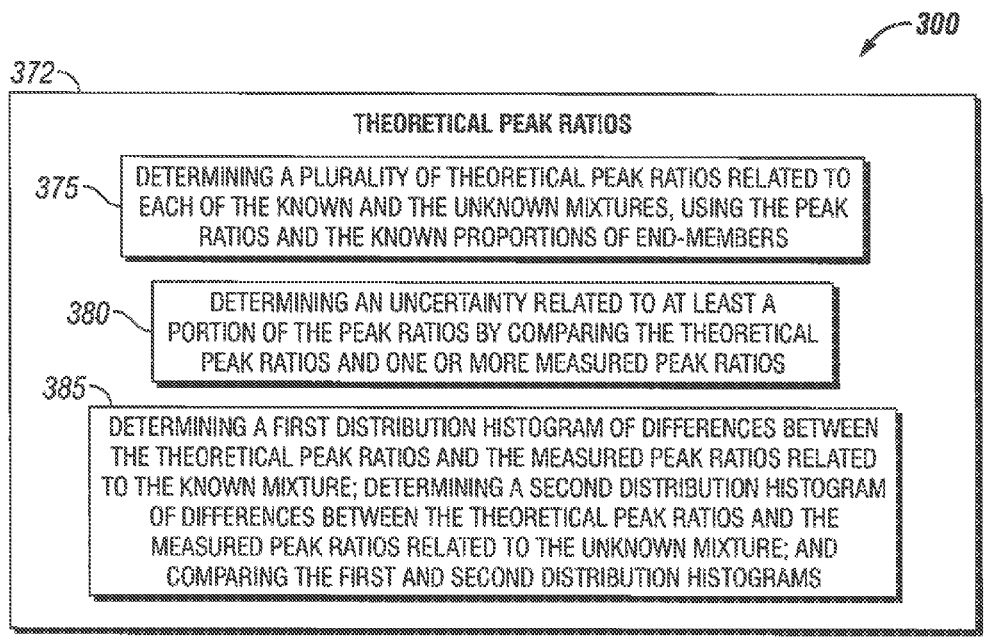

FIG. 3 shows a flowchart of a method 300 according to an example embodiment. The method 300 includes a block 302, which may include estimating unknown proportions of end members. Block 302 may include blocks 305, 315, 320 and 325, as described hereafter. Block 305 may include providing a known mixture including a known proportion of a plurality of end-members, and an unknown mixture including unknown proportions of the end-members. Block 315 may include performing a first chromatographic analysis of each of the known mixture, the end-member, and the unknown mixture. Block 320 may include determining a plurality of peak ratios, and prior peak ratio qualities related to the peak ratios, using the chromatographic analysis. Block 325 may include estimating an estimate of the unknown proportions of the end-members using the peak ratios, the prior peak ratio qualities, and the known proportion of the end-members.

The method 300 may also include a block 328, which may include performing additional chromatographic analyses. Block 328, may include blocks 330, 332, 334, and 336, as described hereafter. Block 330 may include performing a second chromatographic analysis of at least one of: the known mixture, or the end-member (wherein the chromatographic analysis of block 315 includes a first chromatographic analysis). Block 332 may include identifying a first peak ratio of the peak ratios, wherein the first peak ratio is common to the first and second chromatographic analysis. Block 334 may include determining a first prior peak ratio quality related to the first peak ratio, based on a comparison of the first and second chromatographic analyses. Block 336 may include estimating a noise estimation, using the chromatographic analysis, and determining a first of the prior peak ratio qualities, using the noise estimation.

Furthermore, the method 300 may include a block 340, which may include performing an optimization method. Block 340 may include blocks 350 and 352, as described hereafter. Block 350 may include determining a plurality of posterior peak ratio qualities related to the plurality of peak ratios, using the peak ratios, the prior peak ratio qualities, and the known proportions of the end-members. Block 352 may include estimating a second estimate of the unknown proportions of the end-members by iteratively using the peak ratios, the posterior peak ratio qualities, and the known proportions of the end-members, until a quadratic difference between the prior peak ratio qualities and the posterior peak ratio qualities is less than a predetermined threshold.

Method 300 may include block 354, which may include performing an uncertainty calculation. Block 354 may include blocks 355, 365, and 370, as described hereafter. Block 355 may include generating a plurality of peak ratio datasets by randomly drawing a portion of the peak ratios at a time with replacement. Block 365 may include estimating a plurality of second estimates of the unknown proportions of the end-members for each peak ratio dataset (wherein the estimate of the unknown proportions includes a first estimate of the unknown proportions). Block 370 may include determining an uncertainty related to the first estimate of the unknown proportions by calculating a covariance matrix using the second estimates of the unknown proportions.

Method 300 may also include block 372, which may include determining theoretical peak ratios. Block 372 may include block 375, 370, and 385, as described hereafter. Block 375 may include determining a plurality of theoretical peak ratios related to each of the known and the unknown mixtures, using the peak ratios and the known proportions of end-members. Block 380 may include determining an uncertainty related to at least a portion of the peak ratios by comparing the theoretical peak ratios and one or more measured peak ratios. Block 385 may include determining a first distribution histogram of differences between the theoretical peak ratios and the measured peak ratios related to the known mixture; determining a second distribution histogram of differences between the theoretical peak ratios and the measured peak ratios related to the unknown mixture; and comparing the first and second distribution histograms.

The method 300 as shown in FIG. 3 may be implemented with various computer-readable media (CRM). Such CRM may generally include instructions suitable for execution by one or more processors (or cores) to instruct a computing device or system to perform one or more actions related to a method (e.g., method 300 described above). While various blocks are shown, a single medium may be configured with instructions to allow for, at least in part, performance of various actions of the method 300.

Computer System

Figure 4:
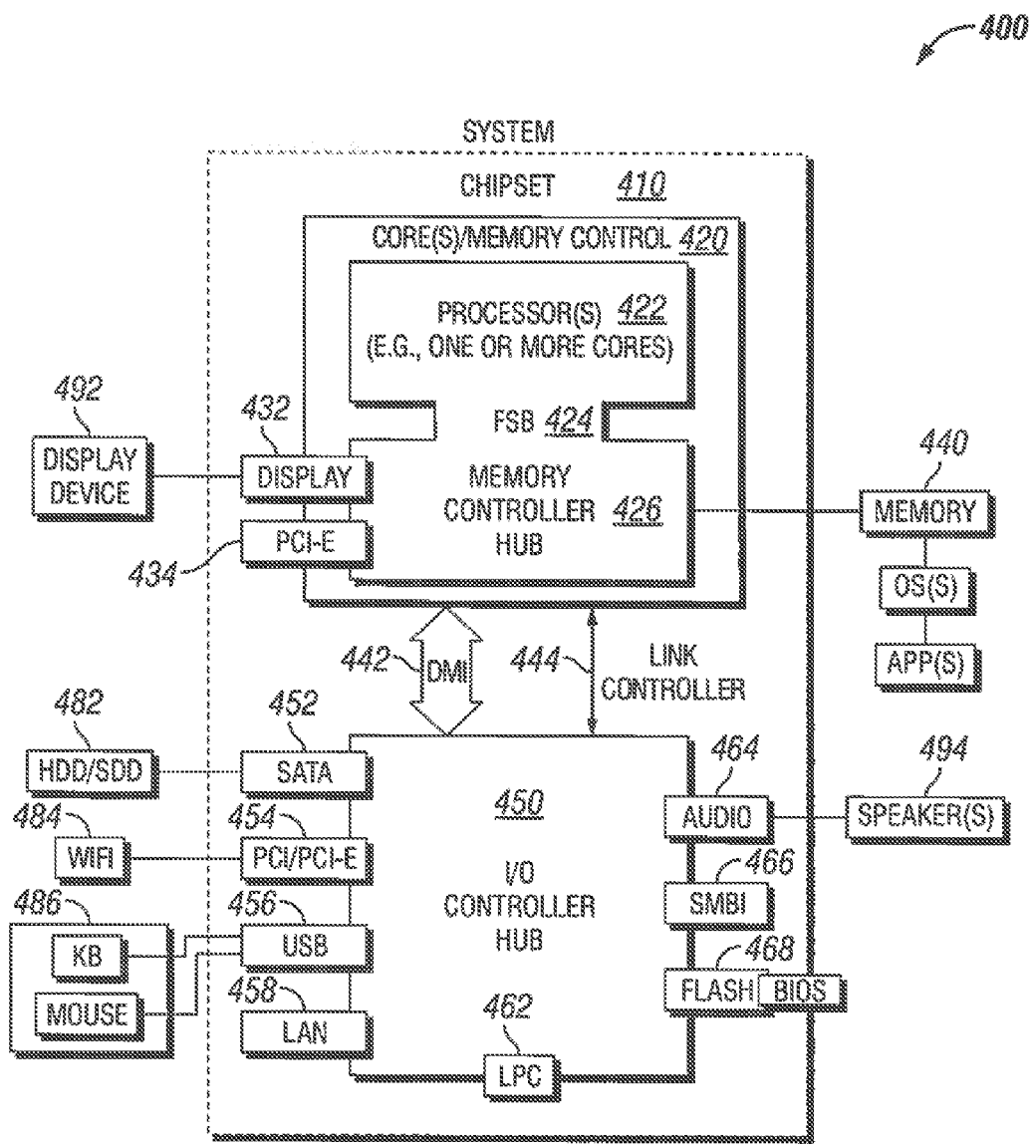
FIG. 4 shows a schematic diagram of a computer system according to an example embodiment.

FIG. 4 shows a system 400 that may be used to execute software containing instructions to implement example embodiments according to the present disclosure. The system 400 of FIG. 4 may include a chipset 410 that includes a core and memory control group 420 and an I/O controller hub 450 that exchange information (e.g., data, signals, commands, etc.) via a direct management interface (e.g., DMI, a chip-tochip interface) 442 or a link controller 444. The core and memory control group 420 include one or more processors 422 (e.g., each with one or more cores) and a memory controller hub 426 that exchange information via a front side bus (FSB) 424 (e.g., optionally in an integrated architecture). The memory controller hub 426 interfaces with memory 440 (e.g., RAM "system memory"). The memory controller hub 426 further includes a display interface 432 for a display device 492. The memory controller hub 426 also includes a PCI-express interface (PCI-E) 434 (e.g., for graphics support).

In FIG. 4, the I/O hub controller 450 includes a SATA interface 452 (e.g., for HDDs, SDDs, etc., 482), a PCI-E interface 454 (e.g., for wireless connections 484), a USB interface 456 (e.g., for input devices 486 such as keyboard, mice, cameras, phones, storage, etc.), a network interface 458 (e.g., LAN), a LPC interface 462 (e.g., for ROM, I/O, other memory), an audio interface 464 (e.g., for speakers 494), a system management bus interface 466 (e.g., SM/I2C, etc.), and Flash 468 (e.g., for BIOS). The I/O hub controller 150 may include gigabit Ethernet support.

The system 400, upon power on, may be configured to execute boot code for BIOS and thereafter processes data under the control of one or more operating systems and application software (e.g., stored in memory 440). An operating system may be stored in any of a variety of locations. A device may include fewer or more features than shown in the example system 400 of FIG. 4.

CONCLUSION

Although various methods, devices, systems, etc., have been described in language specific to structural features and/or methodological acts, it is to be understood that the subject matter defined in the appended claims is not necessarily limited to the specific features or acts described. Rather, the specific features and acts are disclosed as examples of forms of implementing the claimed methods, devices, systems, etc.

What is claimed is:

1. A method, comprising:
providing a known mixture comprising known proportions of a plurality of end-members;
providing an unknown mixture comprising unknown proportions of the end-members;
performing a chromatographic analysis of each of the known mixture, the end-members, and the unknown mixture;
determining, by operation of a processor, a plurality of peak ratios, and prior peak ratio qualities related to the peak ratios, using the chromatographic analysis; and
estimating, by operation of the processor, an estimate of the unknown proportions of the end-members using the peak ratios, the prior peak ratio qualities, and the known proportions of the end-members.

2. The method of claim 1, wherein the chromatographic analysis comprises a first chromatographic analysis, and further comprising:
performing a second chromatographic analysis of at least one of: the end-members or the known mixture;
identifying a first peak ratio of the peak ratios, wherein the first peak ratio is common to the first and second chromatographic analysis; and
determining a first prior peak ratio quality related to the first peak ratio, based on the first and second chromatographic analyses.

3. The method of claim 1, wherein determining the prior peak ratio qualities comprises:
estimating a noise estimation, using the chromatographic analysis; and
determining a first of the prior peak ratio qualities, using the noise estimation.

4. The method of claim 1, further comprising:
determining a plurality of posterior peak ratio qualities related to the plurality of peak ratios, using the peak ratios, the prior peak ratio qualities, and the known proportions of the end-members; and
estimating a second estimate of the unknown proportions of the end-members by iteratively using the peak ratios, the posterior peak ratio qualities, and the known proportions of the end-members, until a quadratic difference between the prior peak ratio qualities and the posterior peak ratio qualities is less than a predetermined threshold.

5. The method of claim 1, wherein the estimate of the unknown proportions comprises a first estimate of the unknown proportions, and further comprising:
generating a plurality of peak ratio datasets by randomly drawing a portion of the peak ratios at a time with replacement;
estimating a plurality of second estimates of the unknown proportions of the end-members for each peak ratio dataset; and
determining an uncertainty related to the first estimate of the unknown proportions by calculating a covariance matrix using the second estimates of the unknown proportions.

6. The method of claim 1, further comprising:
determining a plurality of theoretical peak ratios related to each of the known and the unknown mixtures, using the peak ratios and the known proportions of end-members; and
determining an uncertainty related to at least a portion of the peak ratios by comparing the theoretical peak ratios and one or more measured peak ratios.

7. The method of claim 6, further comprising:
determining a first distribution histogram of differences between the theoretical peak ratios and the measured peak ratios related to the known mixture;
determining a second distribution histogram of differences between the theoretical peak ratios and the measured peak ratios related to the unknown mixture; and
comparing the first and second distribution histograms.

8. One or more non-transitory computer-readable media for processing data, the computer-readable media comprising computer-executable instructions to instruct a computing device to perform a process, the process comprising:
performing a chromatographic analysis of each of a known mixture comprising known proportions of a plurality of end members, an unknown mixture comprising unknown proportions of the end members, and the end-members;
determining a plurality of peak ratios, and prior peak ratio qualities related to the peak ratios, using the chromatographic analysis; and
estimating an estimate of the unknown proportions of the end-members using the peak ratios, the prior peak ratio qualities, and the known proportions of the end-members.

9. The one or more non-transitory computer-readable media of claim 8, wherein the chromatographic analysis comprises a first chromatographic analysis, and the process further comprising:
performing a second chromatographic analysis of at least one of: the end-members or the known mixture;
identifying a first peak ratio of the peak ratios, wherein the first peak ratio is common to the first and second chromatographic analysis; and determining a first prior peak ratio quality related to the first peak ratio, based on the first and second chromatographic analyses.

10. The one or more non-transitory computer-readable media of claim 8, wherein determining the prior peak ratio qualities comprises:
estimating a noise estimation, using the chromatographic analysis; and
determining a first of the prior peak ratio qualities, using the noise estimation.

11. The one or more non-transitory computer-readable media of claim 8, the process further comprising:
determining a plurality of posterior peak ratio qualities related to the plurality of peak ratios, using the peak ratios, the prior peak ratio qualities, and the known proportions of the end-members; and
estimating a second estimate of the unknown proportions of the end-members by iteratively using the peak ratios, the posterior peak ratio qualities, and the known proportions of the end-members, until a quadratic difference between the prior peak ratio qualities and the posterior peak ratio qualities is less than a predetermined threshold.

12. The one or more non-transitory computer-readable media of claim 8, wherein the estimate of the unknown proportions comprises a first estimate of the unknown proportions, and the process further comprising:
generating a plurality of peak ratio datasets by randomly drawing a portion of the peak ratios at a time with replacement;
estimating a plurality of second estimates of the unknown proportions of the end-members for each peak ratio dataset; and determining an uncertainty related to the first estimate of the unknown proportions by calculating a covariance matrix using the second estimates of the unknown proportions.

13. The one or more non-transitory computer-readable media of claim 8, the process further comprising:
determining a plurality of theoretical peak ratios related to each of the known and the unknown mixtures, using the peak ratios and the known proportions of end-members; and
determining an uncertainty related to at least a portion of the peak ratios by comparing the theoretical peak ratios and one or more of the peak ratios.

14. The one or more non-transitory computer-readable media of claim 13, the process further comprising:
determining a first distribution histogram of differences between the theoretical peak ratios and the measured peak ratios related to the known mixture;
determining a second distribution histogram of differences between the theoretical peak ratios and the measured peak ratios related to the unknown mixture; and
comparing the first and second distribution histograms.

15. A system for processing data, comprising:
a processor;
a memory;
a storage medium;
a plurality of computer-executable instructions residing in the storage medium to instruct the processor to perform a process, the process comprising:
performing a chromatographic analysis of each of a known mixture comprising known proportions of a plurality of end members, an unknown mixture comprising unknown proportions of the end members, and the end-members;
determining a plurality of peak ratios, and prior peak ratio qualities related to the peak ratios, using the chromatographic analysis; and
estimating an estimate of the unknown proportions of the end-members using the peak ratios, the prior peak ratio qualities, and the known proportions of the end-members.

16. The system of claim 15, wherein the chromatographic analysis comprises a first chromatographic analysis, and the process further comprising:
performing a second chromatographic analysis of at least one of: the end-members or the known mixture;
identifying a first peak ratio of the peak ratios, wherein the first peak ratio is common to the first and second chromatographic analysis; and
determining a first prior peak ratio quality related to the first peak ratio, based on the first and second chromatographic analyses.

17. The system of claim 15, wherein determining the prior peak ratio qualities comprises:
estimating a noise estimation, using the chromatographic analysis; and
determining a first of the prior peak ratio qualities, using the noise estimation.

18. The system of claim 15, the process further comprising:
determining a plurality of posterior peak ratio qualities related to the plurality of peak ratios, using the peak ratios, the prior peak ratio qualities, and the known proportions of the end-members; and
estimating a second estimate of the unknown proportions of the end-members by iteratively using the peak ratios, the posterior peak ratio qualities, and the known proportions of the end-members, until a quadratic difference between the prior peak ratio qualities and the posterior peak ratio qualities is less than a predetermined threshold.

19. The system of claim 15, wherein the estimate of the unknown proportions comprises a first estimate of the unknown proportions, and the process further comprising:
generating a plurality of peak ratio datasets by randomly drawing a portion of the peak ratios at a time with replacement;
estimating a plurality of second estimates of the unknown proportions of the end-members for each peak ratio dataset; and
determining an uncertainty related to the first estimate of the unknown proportions by calculating a covariance matrix using the second estimates of the unknown proportions.

20. The system of claim 15, the process further comprising:
determining a plurality of theoretical peak ratios related to each of the known and the unknown mixtures, using the peak ratios and the known proportions of end-members; and
determining an uncertainty related to at least a portion of the peak ratios by comparing the theoretical peak ratios and one or more measured peak ratios;
determining a first distribution histogram of differences between the theoretical peak ratios and the measured peak ratios related to the known mixture;
determining a second distribution histogram of differences between the theoretical peak ratios and the measured peak ratios related to the unknown mixture; and
comparing the first and second distribution histograms.

* * * * *